US 8,803,509 B2

(12) United States Patent
Ravindran et al.

(10) Patent No.: US 8,803,509 B2
(45) Date of Patent: Aug. 12, 2014

(54) MODULAR NANO AND MICROSCALE SENSORS

(75) Inventors: Ramasamy Ravindran, Atlanta, GA (US); Muhannad Bakir, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 532 days.

(21) Appl. No.: 13/151,148

(22) Filed: Jun. 1, 2011

(65) Prior Publication Data

US 2011/0291643 A1    Dec. 1, 2011

Related U.S. Application Data

(60) Provisional application No. 61/350,051, filed on Jun. 1, 2010.

(51) Int. Cl.
*G01R 1/20* (2006.01)
*G01N 27/327* (2006.01)

(52) U.S. Cl.
CPC .................................. *G01N 27/3278* (2013.01)
USPC ........................... 324/126; 435/287.2; 435/29

(58) Field of Classification Search
CPC ........................................................ G01R 1/20
USPC .......................................................... 324/126
See application file for complete search history.

(56) References Cited

U.S. PATENT DOCUMENTS

2003/0101006 A1* 5/2003 Mansky et al. ................. 702/30
2011/0062531 A1* 3/2011 De Langen et al. ........... 257/414

FOREIGN PATENT DOCUMENTS

WO    WO/2009/138939    * 11/2009    ............ B01L 3/00

* cited by examiner

*Primary Examiner* — Arleen M Vazquez
*Assistant Examiner* — Alesa Allgood
(74) *Attorney, Agent, or Firm* — Troutman Sanders LLP; Ryan A. Schneider; Robert R. Elliott, Jr.

(57) ABSTRACT

Exemplary embodiments of the present invention disclose a modular testing assay. According to various embodiments of the present invention, the sensor arrays, or microplates, are removably attached to a substrate. In some embodiments, the electrical connection between the sensors of the sensor array and the substrate provide for the removal of one sensor array or microplate with another or similar sensor array. The sensor arrays can be aligned using various types of alignment devices or the substrate can be configured to allow various alignments and spatial orientations of one or more sensor arrays.

20 Claims, 9 Drawing Sheets

FIG. 9

MODULAR NANO AND MICROSCALE SENSORS

CROSS REFERENCE TO RELATED APPLICATION

This application claims benefit under 35 U.S.C. §119(e) of U.S. Provisional Patent Application No. 61/350,051 filed 1 Jun. 2010, entitled "Methods for the Packaging and Integration of Advanced Nano and Microscale Sensors with Fluid Delivery Systems and Electronics", which is incorporated by reference as if set forth herein in its entirety.

TECHNICAL FIELD

The present system relates generally to sensor arrays.

BACKGROUND

A vast majority of conventional biological assays deployed in clinical settings rely on the use of labels. Most commonly, these labels are fluorophores. The use of such labels adds to the complexity and limitations of conventional assays in a number of ways. First, detection of the fluorophore requires an optical excitation source that would, at best, be inefficient if made in silicon. Second, the labeling process itself disadvantageously introduces one or more processing steps. Third, the emission spectra of fluorophores, even quantum dots, are so wide that only a limited number can be delineated with certainty in any one test. While methods employing labels do offer excellent sensitivity in applications ranging from confocal microscopy to immunoassays, they do not lend themselves to high-density, on-chip sensing.

The solution to this—one that has been explored with particular vigor over the past decade—is the use of label-free detection. A number of specific approaches are possible, but the general idea of label-free detection is to use a property inherent to the bio-molecule to detect it directly after it has been specifically captured on or near a sensor without the use of additional labels. A target can posses many detectable properties, but most commonly, label-free sensing mainly utilizes two properties—mass and charge. In both cases, the target could specifically be detected at a sensor site through an interaction, such as that between an antigen and antibody or complementary single stranded nucleic acid sequences, or it can be detected non-specifically.

There are several variations of mass-based sensors, but conventionally the mass of the captured target molecule results in the deflection of a cantilever, the alteration of a propagating acoustic wave, or a change in oscillator resonance properties. Charge-based sensors conventionally fall into devices that are field-effect based, where the charge of a captured target modulates the current through the channel of a semiconductor.

BRIEF SUMMARY OF THE DISCLOSURE

Briefly described, the present invention is directed toward a modular testing assay apparatus. In an exemplary embodiment of the present invention, an apparatus is disclosed comprising a re-usable electronics layer comprised of a plurality of sensors on an electronic microplate, or sensor array, and interconnects that communicatively connect the plurality of sensors with the re-usable electronic layer. The electronic microplate is removably affixed to the electronics layer via the interconnects. The electronics layer comprises an electrical communication apparatus that connects to a distal measurement system or detector device such as, but not limited to, a meter. In one exemplary embodiment, the microplate is removable and replaceable with a second microplate. In some examples, the second microplate can have a similar or different sensor configuration. In another exemplary embodiment of the present invention, the electronics layer has a plurality of locations upon which one or more microplates can be placed in various configurations.

In another exemplary embodiment of the present invention, a system is disclosed comprising an assay apparatus comprising an electronics layer, and a plurality of sensor arrays removably installed on the electronics layer, wherein the plurality of sensor arrays comprise a plurality of sensors. The system further comprises a plurality of disconnectable interconnects that communicatively connect one or more of the plurality of sensors with the electronics layer, wherein the plurality of sensors of the plurality of sensor arrays are removably affixed to the electronics layer via the plurality of disconnectable interconnects. The measurement system further comprises a detector device communicatively connected to the electronics layer.

The foregoing summarizes beneficial aspects of the present invention, but is not intended to be reflective of the full scope of the present invention as claimed. Additional features and advantages of the present invention are set forth in the following description, are apparent from the description, or learned by practicing the present invention. Moreover, the foregoing summary and following detailed description are exemplary and explanatory, and are intended to provide further explanation of the present invention as claimed.

BRIEF DESCRIPTION OF THE DRAWINGS

The accompanying drawings, which are incorporated in and constitute a part of this specification, illustrate multiple exemplary embodiments of the present invention and, together with the description, serve to explain the principles of the present invention. They are not intended in any manner to limit the scope of the present invention. Headings provided herein are for convenience only and do not necessarily affect the scope or meaning of the claimed invention.

DETAILED DESCRIPTION

The subject matter of the various embodiments is described with specificity to meet statutory requirements. However, the description itself is not intended to limit the scope of the claimed invention. Rather, it has been contemplated that the claimed invention can be embodied in other ways, to include different steps or elements similar to the ones described in this document, in conjunction with other present or future technologies. Although the term "step" can be used herein to connote different aspects of methods employed, the term should not be interpreted as implying any particular order among or between various steps herein disclosed unless and except when the order of individual steps is explicitly required. The following description is illustrative and non-limiting to any one aspect.

It should also be noted that, as used in the specification and the claims, the singular forms "a," "an" and "the" include plural references unless the context clearly dictates otherwise. For example, reference to a component is intended to also include composition of a plurality of components. Also, in describing preferred embodiments, terminology will be resorted to for the sake of clarity. It is intended that each term contemplates its broadest meaning as understood by those skilled in the art and includes all technical equivalents that operate in a similar manner to accomplish a similar purpose. The terms "comprising" or "containing" or "including" mean that at least the named component is present in the system or apparatus, but does not exclude the presence of other components even if the other such components have the same function as what is named.

It is also to be understood that the mention of one or more method steps does not preclude the presence of additional method steps or intervening method steps between those steps expressly identified. Similarly, it is also to be understood that the mention of one or more components in a system does not preclude the presence of additional components than those expressly identified. To facilitate an understanding of the principles and features of the present invention, embodiments are explained hereinafter with reference to implementation in illustrative embodiments.

In accordance with various embodiments, the presently disclosed invention is a modular testing system or assay apparatus. Various embodiments of the present invention can help reduce costs associated with assaying various substances including, but not limited to, biologics and chemicals, by providing a tester the ability to configure and reconfigure the assay without having to change out the entire assay apparatus.

An issue with conventional assay systems is that the manufacture of the assay assembly can incur significant time and money. Further, the manner in which conventional assays are produced obviate the interchangeability of the sensors. For example, a testing procedure initially can require a large scale mass measurement with a smaller pH measurement requirement. As the testing procedure is optimized, the assay can require an increased accuracy of pH measurements, necessitating an increased number of sensors that can sense pH. Further, there can be additional measurements that need to be performed, but were not known at the time of constructing the assay.

The present invention provides for variable testing assays by providing a modular testing apparatus with interchangeable testing sensor arrays. Various embodiments of the present invention comprise an electronics layer that constitutes a substrate that supports various components of the present invention. For example, the electronics layer provides a "remove and replace" feature of the present invention, wherein various sensor arrays, or electronic microplates, have sensors that can be removed and replaced. Further, in some embodiments, the electronics layer provides a way in which various sensor arrays can be "built up" or augmented with other sensor arrays to provide a more thorough test. For example, in a system in which the pH measurement has been determined to be an increasingly important measurement, more pH sensors on a removable microplate can be installed on the electronics layer, thereby increasing the number of pH sensors. Further, the electronics layer can provide a generic interface in which one or more compliant microplate structures can be interchangeably affixed, thereby changing the assay capabilities without the need to replace or augment the entire assay structure.

Figure 1A:
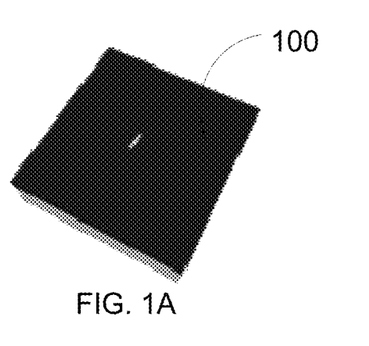
FIGS. 1A-1D are illustrations showing an exemplary fabrication process for a Silicon Nano-wire (SiNW) array.
Figure 1B:
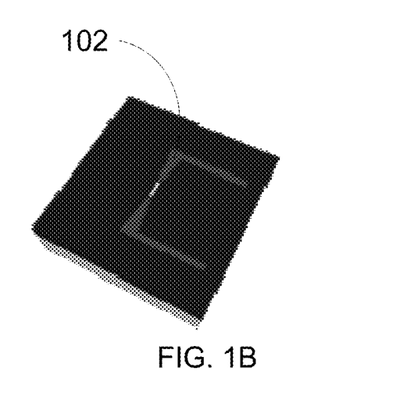
Figure 1C:
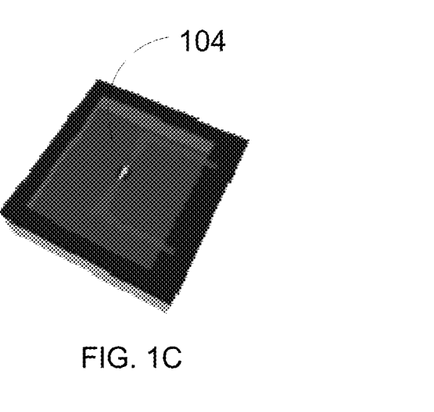
Figure 1D:
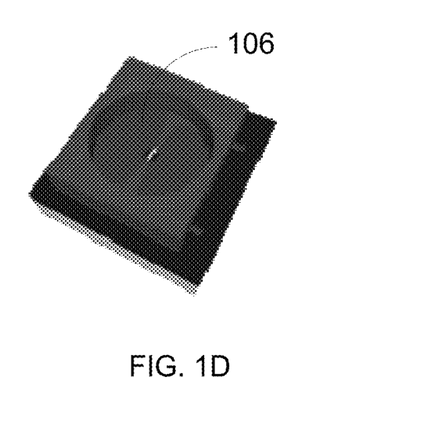

The sensors used in various embodiments of the present invention can vary. A widely used sensor is formed from Silicon Nano-wire structures. FIGS. 1A-1D illustrate an exemplary method of producing an SiNW sensor structure. It should be noted that the present invention is not limited to an SiNW array, as other types of arrays can be used. The SiNW array fabrication process is top-down and CMOS compatible from start to finish. The construction process begins with a silicon-on-insulator (SOI) wafer 100 with a 70 nm thick device layer (p-type, 1-10 Ω-cm) and a 145 nm buried oxide (BOX) layer 102, as shown in FIGS. 1A and 1B. E-beam lithography (EBL) is used to define a 4×4 array of 50 nm wide×70 nm tall×50 μm long SiNWs per 1×1 cm chip 104. It should be noted that this relatively low density of sensors is chosen not because of any inherent process or design limitations, but to facilitate simple manual sample loading via micropipettes for the tests reported herein.

Further, the particular density of sensors should only be viewed as exemplary and not an explicit or implicit limitation on the scope of the present invention. Following EBL, the device layer is anisotropically etched down to the BOX using an Ar/Cl$_2$ plasma in an ICP, in turn forming the SiNWs. The SiNW then undergoes a 900° C. RTP anneal in an O$_2$ ambient to reduce etch damage and grow a thin field oxide. Optical lithography is then used to define Al source and drain electrodes which are subsequently deposited using e-beam evaporation. After lift-off, a 450° C. RTP anneal in forming gas creates ohmic contacts between the Al electrodes and SiNWs 106. To protect the electrodes and define the wells, two layers of SU-8 are deposited. The first 2 μm thick layer protects the electrodes and opens 40×40 μm windows around the SiNWs and the probing pads while the second 100 μm thick layer forms the 1 mm diameter wells 106 into which the samples are loaded.

Figure 2:
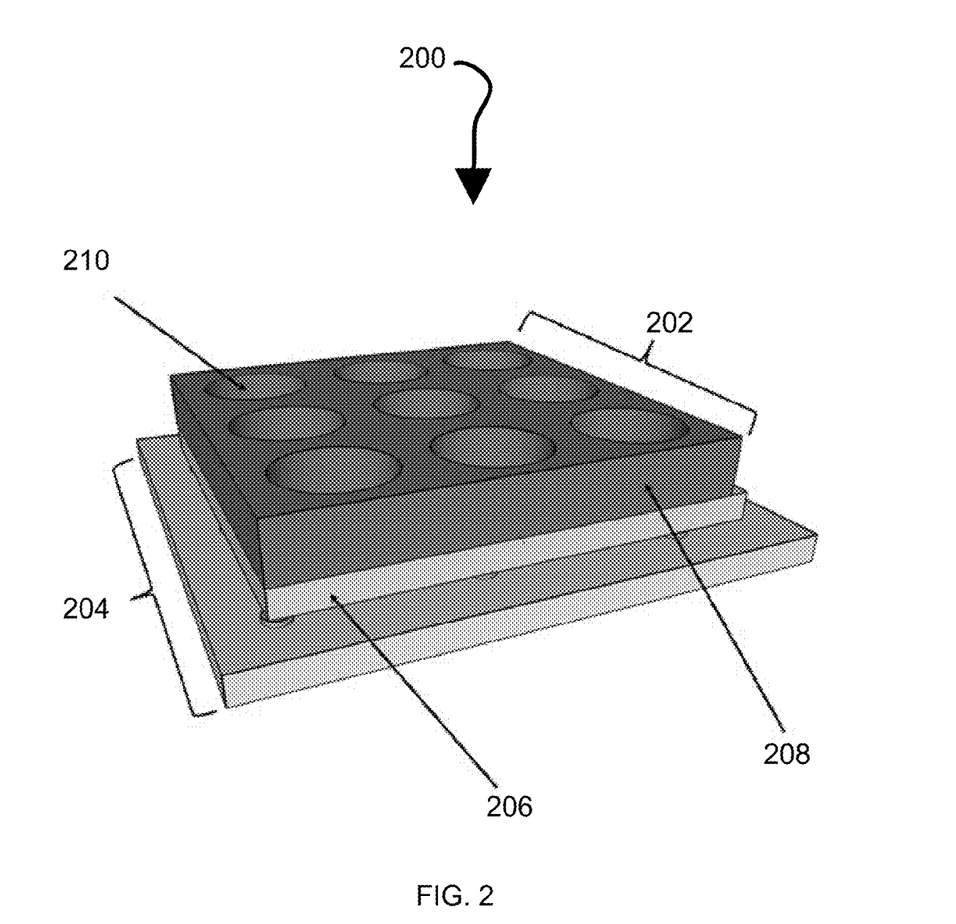
FIG. 2 is a perspective illustration of an exemplary sensor array according to an exemplary embodiment of the present invention.

FIG. 2 illustrates exemplary testing assay 200 according to an exemplary embodiment of the present invention. In accordance with various construction techniques, including the techniques illustrated and described in FIGS. 1A-1D, sensor array 202 is assembled. Sensor array 202 is a "disposable" or "removable" microplate. In some examples, that means sensor array 202 is removably attached to a substrate, shown in FIG. 2 to be electronics layer 204. The sensors 208 of sensor array 202 communicate with a testing device (not shown) via electronics layer 204, which is communicatively connected to the testing device. To isolate samples measured, sensors 208 of sensor array 202 are isolated from each other through the use of wells 210.

Figure 3:
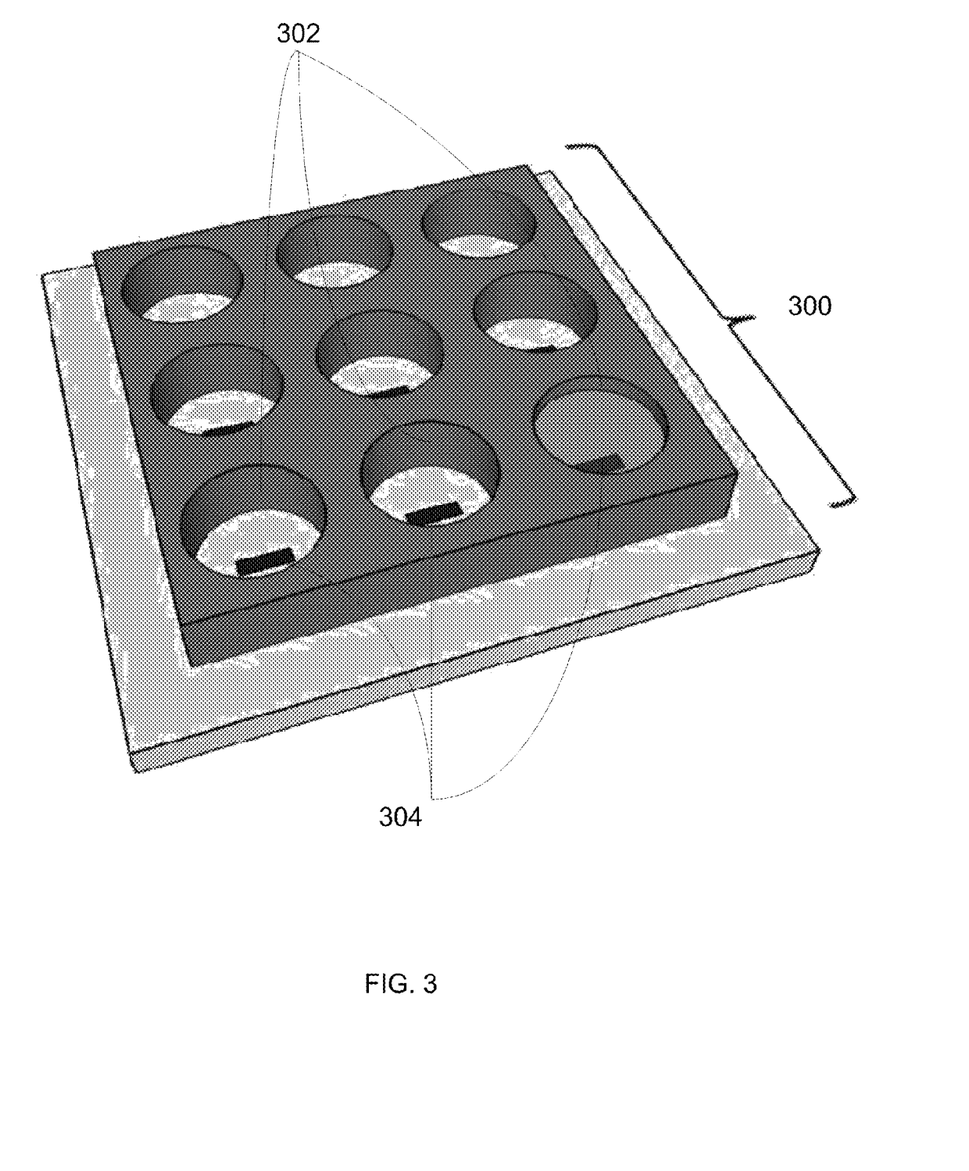
FIG. 3 is a perspective illustration of a sensor according to an exemplary embodiment of the present invention.

FIG. 3 is an illustration showing sensors and a sensor array according to another exemplary embodiment of the present invention. Sensor array 300 comprises a plurality of wells (shown by way of example as wells 302) with sensors 304 at the bottom of wells 302. It should be noted that the present invention is not limited to any particular type of sensor or well configuration. Further, the present invention is not limited to any particular spatial relationship of a sensor/array configuration. For example, sensor 304 can be placed on the sidewall of a well 302, or in other locations within the well 302.

Returning to FIG. 2, in some examples, the testing device can be a meter attached to assay 200 via electronics layer 204, or can be a computer having instructions stored thereon for receiving and outputting measurements provided by the sensors. Interconnect 206 connects one or more of the sensors 208 of sensor array 202 to electronics layer 204. Interconnect 206 comprises a plurality of communication interconnects that connect the sensors 208 of sensor array 202 to electronics layer 204. The manner in which the communication interface is provided can vary. For example, interconnect 206 can have electrical contacts that electrically connect the sensors 208 with electronics layer 204. In another example, interconnect 206 can be waveguides that connect one or more of the sensors 208 of sensor array 202 to electronic layer 204 using light. In another example, interconnect 206 can have liquid flow channels that connect one or more sensors 208 of sensor array 202 to electronic layer 204 via liquid movement. In a still further example, the communication between one or more sensors 208 of sensor array 202 can be combinations of various types of communication, including those not presently disclosed.

Figure 4:
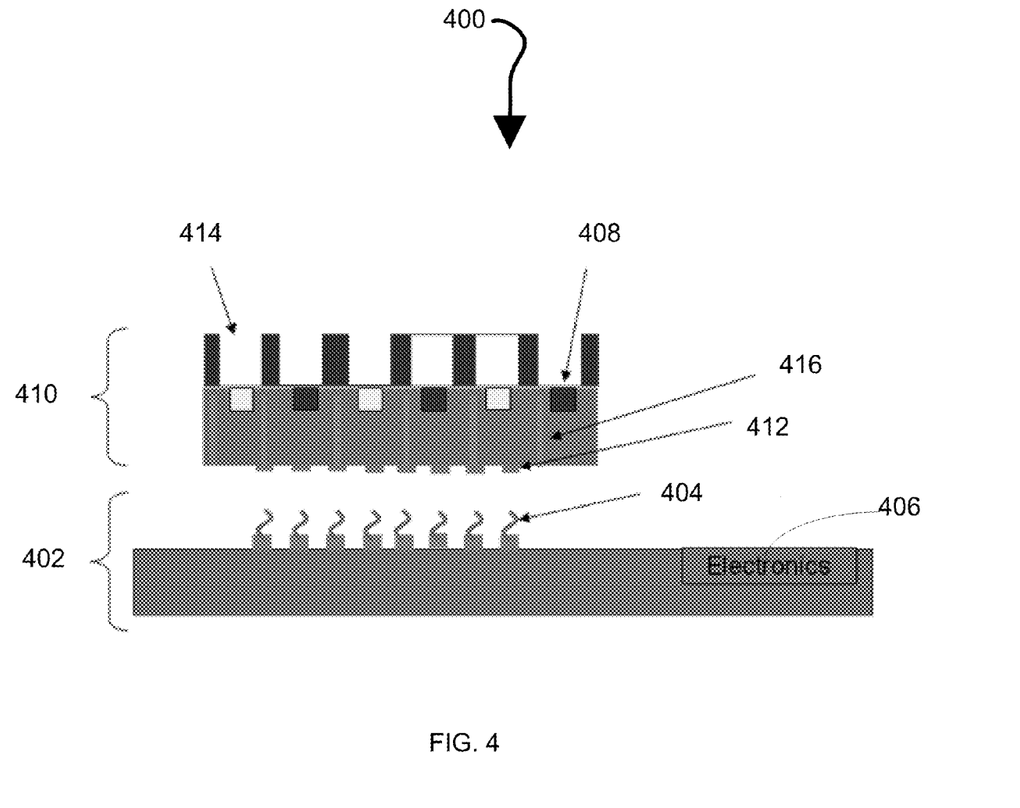
FIG. 4 is an exploded side view illustration of an array according to another embodiment of the present invention.

FIG. 4 is a side view of an exemplary array apparatus 400 according to an exemplary embodiment of the present invention. Substrate 402 has one or more electrical connections 404 and an electronics communication interface 406. Electrical connections 404 connect the electronics communication interface 406 to one or more sensors 408 of sensor array 410 via sensor connects 412 of sensor array 410. Electrical connections 404 can vary in specific type, but should be designed to allow the installation and removal of sensor arrays 410 from substrate 402. Some examples of the types of electrical connections that can be used include, but are not limited to, a ball grid array, electrical leads and a wireless electrical connection. An example of a wireless electrical connection can be an inductive system in which a magnetic or electromagnetic apparatus detects magnetic or electrical changes with the sensor without the need for a physical connection between the sensor connect 412 and electrical connections 404. Sensors 408 can be separated from each other by the use of one or more wells 414 that provide a level of physical separation between sensors 408. In one example of the present invention, through vias 416 communicatively connect one or more sensors 408 to sensor connects 412.

Figure 5:
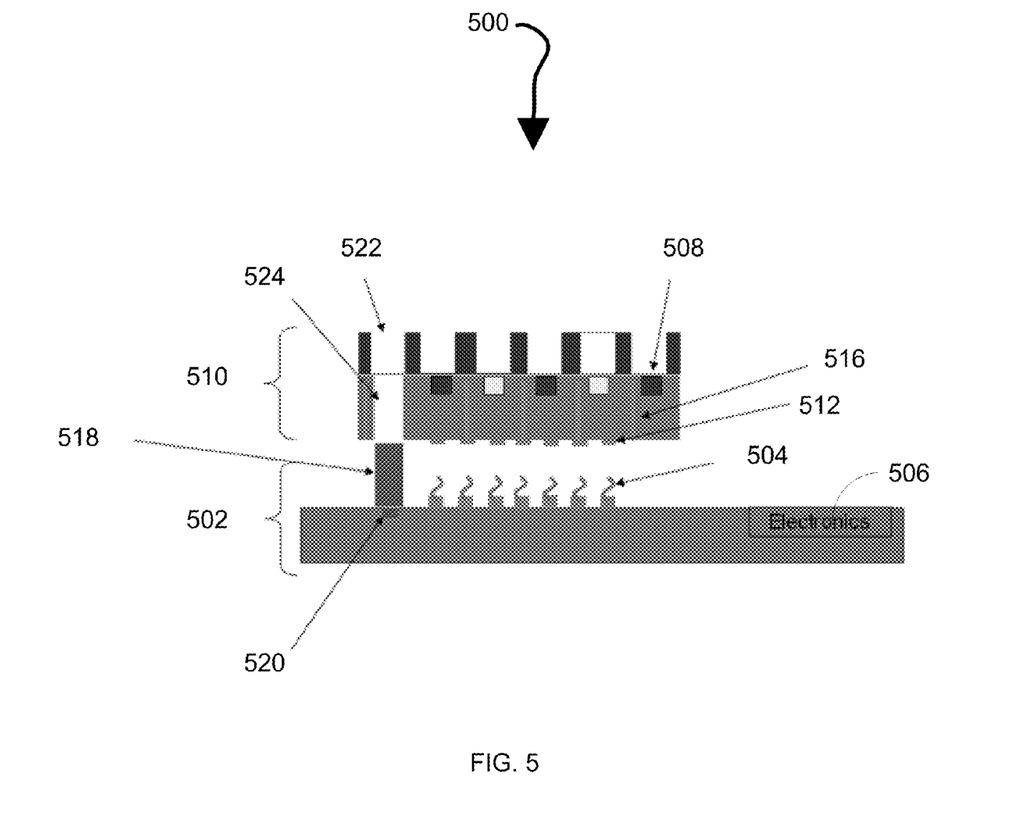
FIG. 5 is an exploded side view of a sensor array according to an alternate exemplary embodiment of the present invention.

FIG. 5 is a side view of an exemplary array apparatus 500 according to another embodiment of the present invention. Substrate 502 has one or more electrical connections 504 and an electronics communication interface 506. Electrical connections 504 connect the electronics communication interface 506 to one or more sensors 508 of sensor array 510 via sensor connects 512 of sensor array 510. Electrical connections 504 can vary in specific type, but should be designed to allow the installation and removal of sensor arrays 510 from substrate 502. Some examples of the types of electrical connections that can be used include, but are not limited to, a ball grid array and electrical leads. In one example of the present invention, through vias 516 communicatively connect one or more sensors 508 to sensor connects 512. As previously discussed, various types of sensors can be used including optical sensors. Optical sensors can be used to detect the translucent or transparent characteristics of a substance, as well as other optical characteristics. In the embodiment illustrated in FIG. 5, an optical input/output waveguide 518 is used to optically connect source/detector 520 with well 522. In this configuration, sensor 520 is optically connected to the material in well 522 through the use of optical through-via 524.

Figure 6:
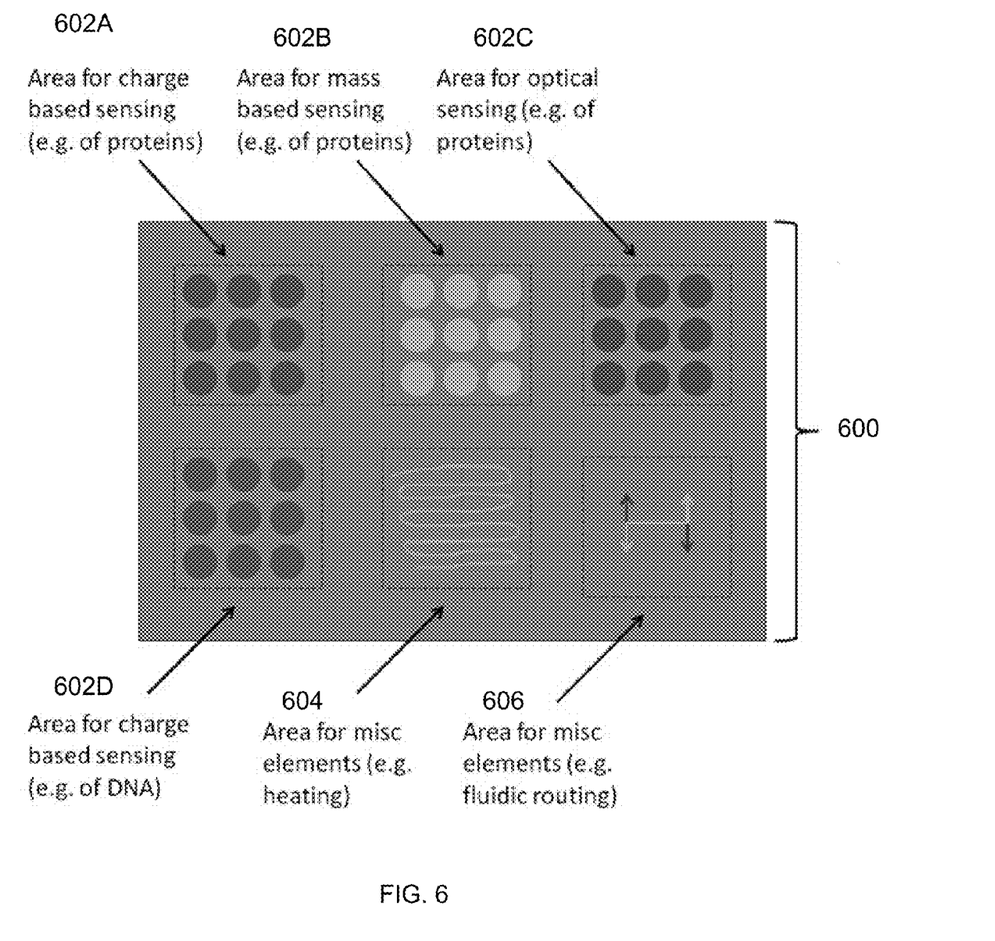
FIG. 6 is a top down illustration of multiple testing areas in an array according to an exemplary embodiment of the present invention.

In some embodiments of the present invention, a sensor array can be assembled using interchangeable sensor arrays to form one sensor measurement apparatus 600. FIG. 6 illustrates multiple sensor arrays 602 A-D that can be used in accordance with an exemplary embodiment of the present invention. Shown are sensor 602A for protein charged-based sensing, sensor 602B for mass-based sensing, sensor 602C for optical sensing and sensor 602D for DNA charged-based sensing. Sensors 602A-D can be removed and replaced with similar or alternate sensors to tailor sensor measurement apparatus 600 to a particular function. Additionally, sensor measurement apparatus 600 can be configured with supporting and/or auxiliary functions as well. Heating elements 604 can be installed to provide heating to an area of the sensor measurement apparatus 600. Further, miscellaneous elements, shown as area 606, can be installed to provide functions such as fluid routing. It should be noted that sensor measurement apparatus 600 can also be a single sensor array, such as an array that can be formed on a single silicon chip.

Figure 7:
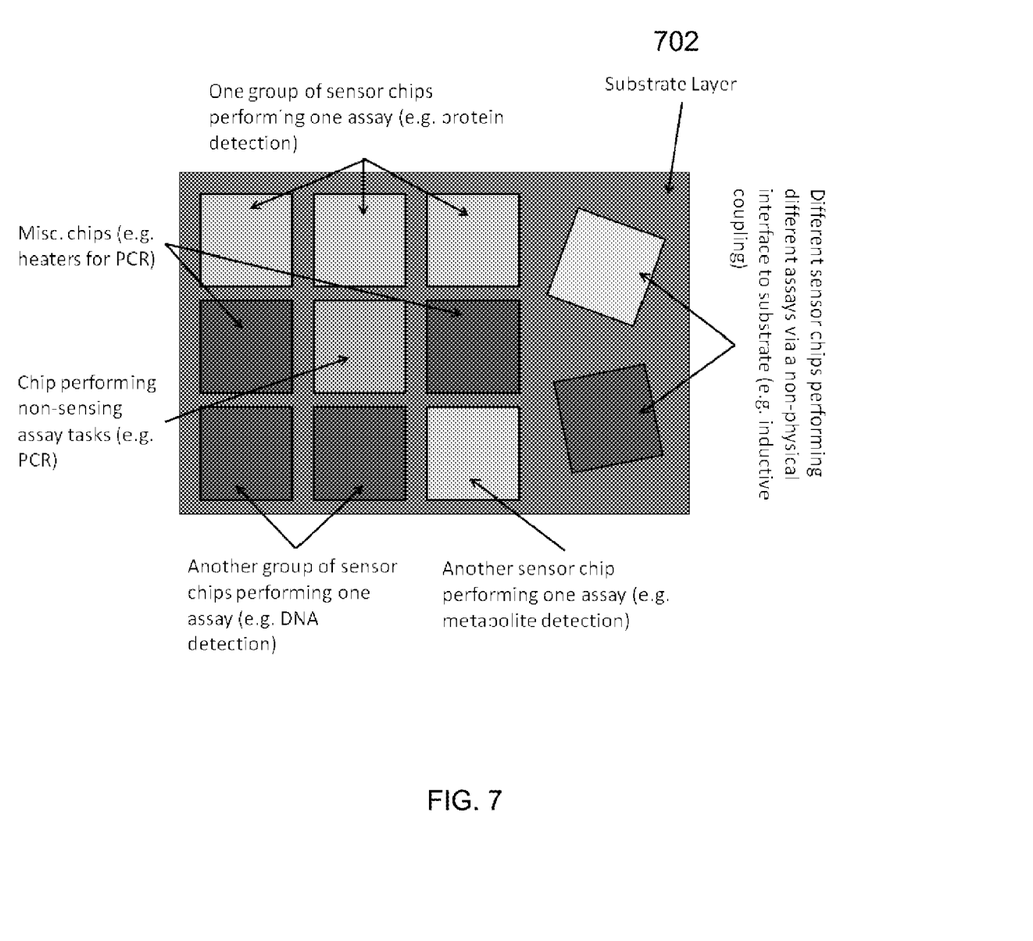
FIG. 7 is a top down illustration of multiple testing areas in an array according to another exemplary embodiment of the present invention.
Figure 8:
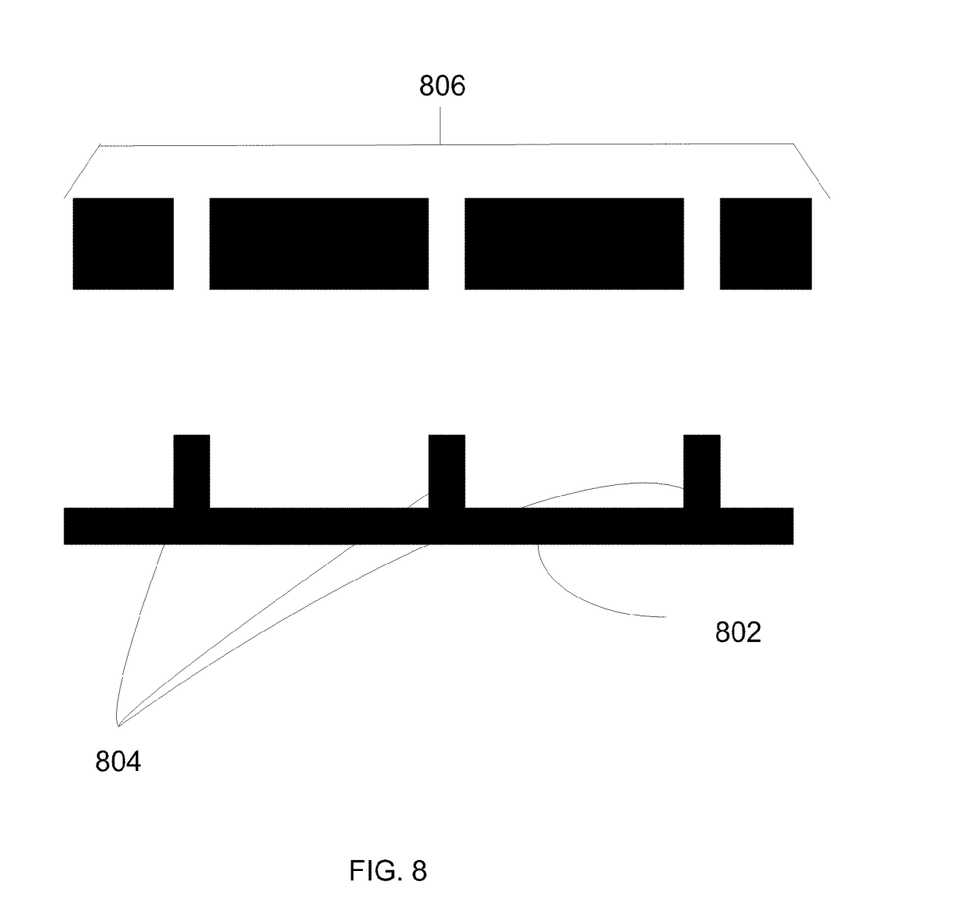
FIG. 8 is a side view illustration of alignment devices used in conjunction with an embodiment of the present invention.

It should be noted that the present invention is not limited to any particular size or spatial orientation for sensors that can be installed on a substrate. FIG. 7 illustrates multiple sensors placed on substrate 702. If a particular alignment or spatial orientation of the sensors of a sensor array is desired or needed, FIG. 8 illustrates one way in which the alignment can be accomplished. Illustrated are alignment devices 804 that physically align sensor array 806 for installation on substrate 802. Alignment devices 804 are shown to be physical "pegs" inserted into sensor array 806.

Figure 9:
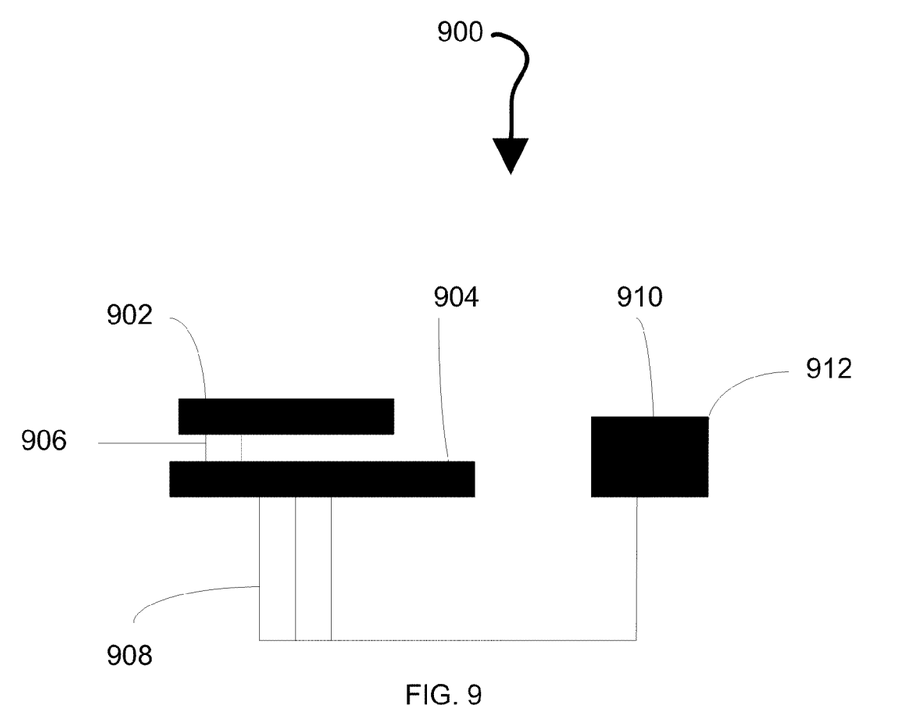
FIG. 9 is an illustration of a system according to an exemplary embodiment of the present invention.

The present invention may be used to test various characteristics of one or more substances. Often, a researcher will need to use an external device to perform certain functions, such as initiating the testing process, energizing the sensors, and/or recording data. FIG. 9 is an exemplary system 900 that can be used in conjunction with an assay apparatus according to various embodiments of the present invention. Removable and replaceable sensor array 902 is communicatively connected to substrate 904 via electrical connection 906. The sensors (not shown) of sensor array 902 provide various types of outputs that are detected by detector device 910 through communication pathway 908 from substrate 904. Detector device 910 can be a computer, a monitor, a meter, or other type of device configured to receive signals from the sensors of sensor array 902.

Further, in some embodiments of the present invention, detector device 910 can also be used to configure sensor array 902 or substrate 904 for use. For example, in some embodiments, detector device 910 can be used to determine various operational characteristics of sensor array 904 such as, but not limited to, the type of sensors being used on sensor array 902. Although it may be preferable that sensor array 902 be marked in some manner to indicate to a researcher or user the types of sensors installed on sensor array 902, these markings can be removed or sensor array may not have had any markings when originally constructed. Further, by detecting the type of sensor on sensor array 902, detector device 910 can help the user by providing an indication of the sensor types and their locations on sensor array 902.

In still further embodiments, an "automatic" installation process may be desirable. For example, even though detector device 910 can determine the type of sensor on sensor array 902, different sensors by different manufacturers, though performing the same function, can have variances of outputs that require changes in calibration. Therefore, one or more of the sensors of sensor array 902 can have certain characteristics that, when detected by detector device 910, configure the operation of detector device 910 for the particular sensor. In one example, detector device 910 can access an online or web-based database having calibration inputs. A researcher or user places sensor array 902 on substrate 904 and initiates detector device 910. Detector device 910 has a sensor 912 that receives input regarding one or more sensors (such as resistance or a "tag" in the electronics of the sensor) in sensor array 902. Detector device 910 interfaces with a database, such as, but not limited to, an online database or a database stored on the detector device 910, and retrieves configuration information. Detector device 910 is then reconfigured according to the retrieved configuration information. This process can be done manually or automatically. When sensor array 902 is removed and replaced with a different (or the same) sensor array, detector device 910 detects or senses the replaced sensor array 902 and performs the calibration procedure again.

The presently disclosed embodiments are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. An assay apparatus for sensing at least one characteristic of a target, comprising:
    a plurality of electronic microplates comprising a plurality of sensors;
    an electronics layer for communicating with an output device; and
    one or more interconnects configured to communicatively connect one or more of the plurality of sensors with the electronics layer,
    wherein the plurality of electronic microplates are interchangeably attachable to and detachable from the electronics layer via the one or more interconnects.

2. The assay of claim 1, wherein at least one sensor of the plurality of sensors is a silicon nanowire array.

3. The assay of claim 1, wherein the plurality of sensors are sensors for detecting one or more of a mass, a charge, a biological measurement, or combinations thereof of the target.

4. The assay of claim 1, wherein at least one of the plurality of sensors detect more than one characteristic of the target.

5. The assay of claim 1, wherein at least one of the plurality of sensors is interchangeable with at least one of another of the plurality of sensors.

6. The assay of claim 1, wherein the one or more interconnects comprise at least one of electrical leads, electrical pads, a ball grid array, optical interconnects, wireless interconnects, and fluidic interconnects.

7. The assay of claim 1, wherein:
    the one or more interconnects comprise magnetic interconnects configured to electromagnetically connect one or more of the plurality of sensors with the electronics layer; and
    the plurality of electronic microplates are interchangeably attachable to and detachable from the electronic layer via the magnetic interconnects.

8. The assay of claim 1, wherein the one or more interconnects comprise at least one optical interconnect including a waveguide and configured to optically connect one or more of the plurality of sensors with the electronics layer.

9. The assay of claim 1, further comprising an alignment device that aligns at least one of the plurality of microplates in relation to the electronics layer.

10. The assay of claim 9, wherein the alignment device is one or more of a barrier, well, alignment pin, or combinations thereof.

11. A measurement system for measuring at least one characteristic of a target, comprising:
    an assay apparatus comprising:
    an electronics layer;
    a plurality of sensor arrays comprising a plurality of sensors; and
    one or more interconnects configured to communicatively connect one or more of the plurality of sensors with the electronics layer, wherein the plurality of sensors of the plurality of sensor arrays are interchangeably attachable to and detachable from the electronics layer via the one or more interconnects; and
    a detector device communicatively connected to the electronics layer that determines a type of sensor of at least one of the plurality of sensors.

12. The system of claim 11, wherein at least one of the plurality of sensors detect one or more of a mass, a charge, a biological measurement, or combinations thereof of the target.

13. The system of claim 11, wherein at least one of the plurality of sensor arrays detect more than one component characteristic of the target.

14. The system of claim 11, wherein at least one of the plurality of sensors is interchangeable with at least one of another of the plurality of sensors.

15. The system of claim 11, wherein the detector device comprises a sensor that detects when a sensor of the plurality of sensors is installed or removed on the electronics microplate.

16. The system of claim 11, further comprising a heating element that controls a temperature of at least a portion of the electronics layer.

17. The system of claim 11, wherein the detector device is configured according to a type of sensor installed.

18. The system of claim 11, wherein at least one sensor of the plurality of sensors is a silicon nanowire array.

19. The system of claim 11, wherein the one or more interconnects comprise at least one of electrical leads, electrical pads, a ball grid array, optical interconnects, wireless interconnects, and fluidic interconnects.

20. The system of claim 11, wherein:
    the one or more interconnects comprise magnetic interconnects configured to electromagnetically connect one or more of the plurality of sensors with the electronics layer; and
    the plurality of sensors are interchangeably attachable to and detachable from the electronic layer via the magnetic interconnects.

* * * * *